(12) United States Patent
Dewalt et al.

(10) Patent No.: US 9,128,075 B2
(45) Date of Patent: Sep. 8, 2015

(54) METHOD FOR CONTROLLING THE SENSITIVITY AND RESPONSE POINT OF CHEMICAL TEST KITS FOR METALS IN PAINT AND OTHER MEDIA

(76) Inventors: Frederic G Dewalt, Landenberg, PA (US); David C. Cox, Chevy Chase, MD (US)

( * ) Notice: Subject to any disclaimer, the term of this patent is extended or adjusted under 35 U.S.C. 154(b) by 397 days.

(21) Appl. No.: 13/539,317

(22) Filed: Jun. 30, 2012

(65) Prior Publication Data

US 2014/0004614 A1 Jan. 2, 2014

(51) Int. Cl.
*G01N 31/22* (2006.01)
*G01N 33/84* (2006.01)
*G01N 1/38* (2006.01)
*G01N 1/28* (2006.01)

(52) U.S. Cl.
CPC *G01N 31/22* (2013.01); *G01N 1/38* (2013.01); *G01N 2001/2866* (2013.01); *Y10T 436/25625* (2015.01)

(58) Field of Classification Search
CPC ... G01N 31/22; G01N 33/1813; G01N 33/84; G01N 33/2864; G01N 1/4077; G01N 1/38; G01N 35/08; G01N 33/04; B01F 13/0059; B01L 3/5027

USPC .................................................. 436/77, 179
See application file for complete search history.

(56) References Cited

U.S. PATENT DOCUMENTS 3,934,976 A * 1/1976 Zelaskowski ................... 436/77
5,912,180 A * 6/1999 Stone .............................. 436/77

OTHER PUBLICATIONS

Standard Practice for Use of Qualitative Chemical Spot Test Kits for Detection of Lead in Dry Paint Films Nov. 1995.*

* cited by examiner

*Primary Examiner* — Lyle Alexander
*Assistant Examiner* — Dwan A Gerido

(57) ABSTRACT

A method of changing the response level for any chemical test kits designed for the determination of a metal or compound (such as lead) in paint and other media is disclosed. The invention solves two common problems that exist with using chemical test kits for the detection of lead in paint or other coatings and media: (1) conversion of the paint sample into particles small enough to dissolve the metal in the sample; and, (2) controlling the amount of (paint) sample that gets exposed to the chemicals. This is accomplished by using a coffee grinder or equivalent tool plus a solid (food) product to break up the paint sample into small particles and at the same time dilute the concentration of the metal, while in solid form, down to a level that results in obtaining a positive response at the desired concentration.

25 Claims, No Drawings

METHOD FOR CONTROLLING THE SENSITIVITY AND RESPONSE POINT OF CHEMICAL TEST KITS FOR METALS IN PAINT AND OTHER MEDIA

STATEMENT REGARDING FEDERALLY SPONSORED RESEARCH OR DEVELOPMENT

This invention was made with government support under grant VALTT0001-11 awarded to QuanTech, Inc., by the U.S. Department of Housing and Urban Development, Office of Healthy Homes and Lead Hazard Control. The government has certain rights in the invention.

CROSS-REFERENCE TO RELATED APPLICATIONS

There are no prior applications on controlling the sensitivity and response point of chemical test kits for metals in paint or other coatings or any other prior applications related to this invention.

REFERENCE TO SEQUENCE LISTING, A TABLE, OR A COMPUTER PROGRAM LISTING COMPACT DISC APPENDIX

Not applicable.

BACKGROUND OF THE INVENTION

The invention relates to a method of controlling the concentration level of a potentially harmful metal, such as lead, at which a positive response is obtained when using a chemical test kit for the detection of that potentially harmful metal in paint or other media. A positive response means that the potentially harmful metal is determined to be present in the material being tested. The method is independent of the chemistry on which the test kit is based.

The discussion of this invention focuses on the use of chemical test kits for detection of lead in paint and other coatings. However, the invented method is also applicable to testing any potentially harmful metal using any chemical test kit that has been found to generate a positive response at concentration levels well below a level considered harmful, i.e., a test kit that is too sensitive with respect to a defined action level. The invented method can also be used for detection of potentially harmful metals in any solid medium other than paint or other coatings provided that the medium is not so hard as to damage the grinder which is one of the tools used by the invented method.

According to a report by the President's Task Force on Environmental Health Risks and Safety Risks to Children, approximately 24 million U.S. dwellings were at risk for lead-based paint hazards in 1999 ["Eliminating Childhood Lead Poisoning: A Federal Strategy Targeting Lead Paint Hazards," President's Task Force on Environmental Health Risks and Safety Risks to Children (February 2000)]. The term lead-based paint (LBP) means paint or other surface coatings that contain lead equal to or exceeding a level of 1.0 milligram per centimeter squared or 0.5 percent by weight [Public Law 102-550, Residential Lead-Based Paint Hazard Reduction Act of the Housing and Community Development Act of 1992, Available from Superintendent of 63 Documents, U.S. Government Printing Office, P.O. Box 371954, Pittsburgh, PA 15250-7954; www.access.gpo.gov/su-docs.]. This definition is also given in the Guidelines for the Evaluation and Control of Lead-Based Paint Hazards in Housing, a document often called the HUD Guidelines [HUD- 1539-LBP, U.S. Department of Housing and Urban Development, Washington, DC (July 1995)]. The accurate and efficient identification of LBP in housing is important to the Federal government. For example, identification of LBP in most pre-1978 target housing requires disclosure of that information, if available, to the owner, prospective purchasers, or tenants (42 U.S.C. 4852d, 24 CFR 35.80-98). Also, in certain target housing receiving financial assistance from HUD, or being sold by the Federal government, identification of LBP results in requirements for LBP hazard evaluation and/or control (42 U.S.C. 4822, 24 CFR 35.1-1355). As far back as the early 1970s, chemical test kits were introduced as relatively non-intrusive, potentially cost saving, qualitative methods for determining the presence or absence of LBP while on-site [Vind, H. P. and Drisko, R. W., Field Identification of Weathered Paints, Technical Report TR-766, Naval Civil Engineering Laboratory, Port Hueneme, Calif. (April 1972), 21 pages; Vind, Harold P. and Mathews, C. W., Field Test for Detecting Lead-Based Paint, Technical Note N-1455, Civil Engineering Laboratory, Port Hueneme, Calif. (September 1976), 9 pages].

A (chemical) test using a test kit involves the application of chemical solution to a prepared dry paint film sample, paint chip, paint powder, or painted surface and the subsequent observation of the presence or absence of a characteristic color change [Use of Qualitative Chemical Spot Test Kits for Detection of Lead in Dry Paint Films, Annual Book of ASTM Standards, Standard Practice E 1753, Vol. 04.07, American Society for Testing and Materials, West Conshohocken, Pa. (1998)]. The most commonly used types of test kits for detecting lead in paint and other coatings involve either rhodizonate or sulfide ion. Several U.S. patents and patent applications exist for such test kits [U.S. Pat. Nos. 6,800,485, 6,489,170, 5,558,835, 5,550,061, 5,364,792, 5,330,917, 5,278,075, 5,039,618, U.S. patent application Ser. No. 2011/0283785, U.S. patent application Ser. No. 2003/0203496, and U.S. patent application Ser. No. 2003/0049852] and prepackaged kits covering both of these types are commercially available from a number of suppliers. The first type is based on the reaction of rhodizonate ion with lead II ion; in acidic solution this reaction produces a color change from yellow-orange to pink or red. The other is based on the reaction of sulfide ion, in basic solution with lead II ion; where either solid lead (II) sulfide is created producing a color change to gray or black or a dark colored solution is formed by adding a caustic leach of the sample prior to adding the sulfide ion [U.S. patent application Ser. No. 2011/0283785]. Observation of the characteristic color change is a taken as a positive indicator of the presence of lead in the paint sample tested.

The American Society for Testing and Materials (ASTM) has issued two standards associated with the use of test kits for LBP: ASTM E 1753, Practice for Use of Qualitative Chemical Spot Test Kits for Detection of Lead in Dry Paint Films [Standard Practice E 1753, Vol. 04.07, American Society for Testing and Materials, West Conshohocken, Pa. (1998).] and ASTM E 1828, Guide for Evaluating the Performance Characteristics of Qualitative Chemical Spot Test Kits for Lead in Paint [ASTM Standard E 1828, Annual Book of Standards, Vol. 04.07, American Society for Testing and Materials, West Conshohocken, Pa. (1998)].

Potential advantages to using test kits over other methods of identifying LBP are that they: are inexpensive and rapid; may require minimal operator technique; and may respond to microgram levels of analyte [Luk, K. K., Hodson, L. L., O'Rouke, J. A., Smith, D. S., and Gutknecht, W. F., Investigation of Test Kits for Detection of Lead in Paint, Dust, and Soil, EPA 600/R-93/085, U.S. Environmental Protection Agency, Research Triangle Park, NC (April 1993)]. For a test kit to be suitable for rapid in-field (not in a laboratory) determinations, the steps needed to conduct the test must be practical, simple, inexpensive, and suitable for use by persons with little or no specific training in laboratory procedures.

Various studies have shown that existing test kits are not reliable for identifying LBP [A Field Test of Lead-Based Paint Testing Technologies: Technical Report, EPA 747-R-95-002b (May 1995); Estes, E. D. and Gutknecht, W. F., Workshop Report: Identification of Performance Parameters for Test Kit Measurement of Lead in Paint, EPA 600/R-93/129, U.S. Environmental Protection Agency, Research Triangle Park, NC (June 1993); Gutknecht, W. F., Hodson, L. L., Luk, K. K., Binstock, D. A., Van Hise, C. C., and Turner, A. R., Pilot Field Study for the Assessment of Techniques Used for the Measurement of Lead in Paint, EPA 600/R-97/057, U.S. Environmental Protection Agency, Research Triangle Park, NC (December 1997).]. The main issue is that, while several kits have been shown to reliably produce positive responses at lead levels at or above the Federal regulatory definition of LBP, all of them also generate positive response well below that level. In other words, existing chemical test kits tend to be too sensitive and often generate positive results even when the true level of lead in the paint is well below the level defined as LBP in Federal regulations.

On Apr. 22, 2008, EPA issued a rule (the Renovation, Repair, and Painting Program Final Rule [the RRP Rule]; Federal Register: Apr. 22, 2008, Volume 73, Number 78, pages 21691-21769). The RRP Rule requires the use of lead-safe practices and other actions aimed at preventing lead poisoning. The RRP Rule allows certified renovators to use EPA recognized chemical test kits as a method of determining the presence or absence of LBP for renovators. Specifically, the final rule exempts renovations (from using lead-safe work practices) that affect only components that a certified renovator, using a chemical test kit recognized by EPA, determines are free of LBP. Since there is a cost to using lead safe work practices, an inexpensive method that can successfully determine the presence or absence of LBP is desirable to reduce the cost of renovation. Laboratory analysis of submitted paint samples could be used, but such an approach is considered far too expensive, too time consuming, and requires a certified lead professional to collect the samples. In response to the need, EPA set a goal within the RRP rule to foster the development of a chemical test kit that can reliably be used by a person with minimal training, is inexpensive, provides results within an hour, and is demonstrated to have a false positive rate of no more than 10 percent and a false negative of less than 5 percent at 1.0 milligram/centimeters squared or 0.5 percent by weight. The requirement for both low false positive and low false negative rates is sometimes referred to as a two-sided test (all quantitative laboratory measurements for metals in paints and coatings provide two-sided tests). EPA further stated in the rule that they were confident that improved test kits meeting EPA's benchmarks would be commercially available by September 2010. EPA's Environmental Technology Verification (ETV) Program was set up as the federal vehicle to evaluate the performance of vendor-submitted lead test kits. Currently, no submitted test kit is able to meet the EPA requirements for a 2-sided test. In the interim, a test kit can be EPA-recognized if it meets the negative response criterion of no more than 5 percent false negatives, with 95 percent confidence for paint containing lead at or above the regulated level, 1.0 mg/ milligram/centimeters squared or 0.5 percent by weight. In other words, the interim recognition is being offered by EPA to test kits that can be used as a one-sided test, referred to as a negative screen, where a negative response it highly likely to indicate that no lead is present at or above the definition for LBP. A positive result from such a test kit is interpreted to mean that the presence of LBP is undetermined (and lead safe work practices would be required). The interim recognition will last until EPA publicizes recognition of the first test kit that meets both the negative response and positive response criteria. As of June 2012, three test kits have been given interim recognition (see <http://www.epa.gov/lead/pubs/test-kit.htm>; last accessed Jun. 15, 2012). The fact that there are test kits able to achieve only interim recognition is proof that these chemical test kits tend to be too sensitive and give positive responses at levels well below the Federal definition of LBP.

The invention, use of solid-phase sample dilution to prepare a sample prior to testing using a test kit, addresses the two key problems with current chemical test kits for the determination of the presence or absence of LBP. The first problem is conversion of the paint sample into particles small enough for the acid or base, present in the chemical test kits, to effectively dissolve the lead in the sample and convert all lead present into lead (II) ions. The chemical reactions used in test kits to detect the metal require that the lead in the sample be dissolved in solution so that all the lead is present in ionic form so it can react with test kit chemicals to create a colored complex that is used to signify presence of the metal in the sample undergoing testing. Breaking down a paint sample into small particles is difficult partly because real-world paint samples from housing and other dwellings often have overlayers of acrylic (latex) paint and these layers tend to make the paint gummy or sticky, rendering it hard to break up. In a laboratory setting, there are many tools available to a trained laboratory technician to convert a solid paint sample into small particles, such as freezing the sample and breaking it up in a shatter-box or using a mortar and pestle. In addition, strong acids can be safely used in a laboratory vented hood to digest the sample and put the lead into solution and these strong acids can help compensate for inefficient breakup of the sample. However, in a non-laboratory setting (such as a home) these tools are impractical, potentially hazardous and generally cannot be successfully or safely used by someone other than a qualified laboratory technician.

The second common problem that existing chemical test kits have is controlling the amount of (paint) sample that is exposed to the chemicals in the test kit. For most test kits, the human eye is used as a detector to produce one of two responses to lead present in the sample undergoing testing: a negative, a color change is not observed; and, a positive, a color change is observed. Positive detection of lead occurs when there is sufficient lead (II) ions present to form enough colored complexes with the chemicals present in the test kit to be observable by the eye. In addition to the color change itself, the degree of color change is sometimes used to help make more accurate negative and positive assessments, generally taking the form of using a colored or shaded standard to use for comparison in a manner that is similar to using pH paper to determine the pH of a solution. However, adjusting the lead level in the paint at which a color change can be observed, by means of a change in the test kit chemicals, is difficult. Since most test kits tend to be too sensitive, the only practical method of obtaining an observable color change at a higher lead level is to reduce the number of lead (II) ions exposed to the chemicals through a reduction in the amount of sample that is undergoing testing. In a laboratory setting, this is generally done by diluting a dissolved (liquid) paint sample until the number of lead (II) ions present in the tested sample is within the concentration operating range of the analytical technique used to measure the amount of lead in the diluted (liquid) sample. Another common laboratory method is to dissolve a sub-sample of the paint sample (by mass) after it has been broken down into smaller particles (discussed under the first problem above). Use of liquid serial dilution methods in the field is impractical, costly, and likely well beyond most persons who are not qualified laboratory technicians. Likewise, the sub-sampling approach is also impractical as it requires the collection of whole sample and sub-sample masses using a high quality analytical scale, again requiring expensive equipment and laboratory level training Current and past test kits have attempted to reduce the number of lead (II) ions exposed to the chemicals by reducing the amount of paint being measured through the use of coring tools with specific diameters and various paint sample slicing methods where specific widths and lengths of paint are exposed to the test kit chemicals. Both these approaches suffer from an inherent problem with using a smaller collected paint sample, i.e., if the collected sample is too small, it may not be representative of the surface material that is being evaluated for lead content. For example, the D-Lead kit presented in U.S. patent application Ser. No. 2011/0283785, uses a 3/16 inch diameter coring tool to obtain a small sample of paint to be exposed to the chemical reagents used in the kit. Given the variable thickness often found in paint and coatings, caused by typical painting techniques, this small diameter (representing an area of only 0.18 centimeters squared) can easily fail to collect a representative sample. In addition, as evidenced by the fact that this kit was unable to meet all the EPA RRP Rule requires, this paint sample size is still too large to reliably determine the presence of LBP (see the estimated false positive rates of 16-29 percent quoted in the application). Using the invention presented here, it is estimated that the area of the sample for the D-Lead kit would have to be reduced by more than a factor if 4 to have a chance at meeting the EPA's less than 10 percent false positive rate criterion. Such a small sample (less than 0.1 inches in diameter) would be hopelessly unrepresentative, and collecting it with the needed repetitive accuracy inherently impractical. As of June 2012, none of the approaches used by test kit manufacturers have been successful as proven by the inability of any of the test kits to achieve two-sided performance requirements set forth by EPA in the RRP Rule.

BRIEF SUMMARY OF THE INVENTION

The invention embodies the use of solid-phase sample dilution wherein a solid medium is used to dilute a paint sample to prepare it for use in detecting the amount of lead (Pb) in the paint sample and wherein the sensitivity of the chemical test kit is reduced such that the level of lead which at which the test kit provides a positive response is increased thereby permitting the use of existing or new chemical test kit technologies. The invention utilizes commonly available inexpensive kitchen tools and solid (food) products to prepare a paint sample using solid-phase sample dilution which solves the two common problems that currently exist with using chemical test kits: (1) conversion of the paint sample into particles small enough to effectively dissolve the metal (lead) in the sample; and, (2) controlling the amount of (paint) sample that is exposed to the chemicals in the test kit so that the observation of a positive response occurs at the desired concentration or Federal action level for LBP. Solid-phase sample dilution is accomplished by placing a sample with known surface area into a coffee grinder (or equivalent tool) plus a measured fixed volume of solid (food) product to break up the paint sample into small particles and, at the same time, accomplish a controlled fixed dilution of the concentration of the lead, while still in solid form, down to a level that results in obtaining a positive response at the desired definition for LBP in the original sample, but not below that level.

BRIEF DESCRIPTION OF THE SEVERAL VIEWS OF THE DRAWING

Not applicable.

DETAILED DESCRIPTION OF THE INVENTION

To address the two common problems discussed in the background section, the invention uses solid-phase sample dilution as an in-field practical, low-cost method to produce an optimally diluted ground sample material to be tested using chemicals from a test kit. The invented method includes the following four basic steps:

(1) Collect a paint sample from the surface undergoing testing using a circular or defined rectangular surface area, or known mass.

(2) Place a specific measured volume of solid (food) product into a small clean coffee grinder or equivalent. Solid food, readily available at any grocery store for minimal cost, is the desired medium to be used to effectively dilute the paint sample while still in solid form before chemicals from a test kit are used to dissolve the metal (lead) and make a determination of the amount of metal (lead) present in the paint sample. Because solid food is fit for human consumption, it is highly unlikely to have enough background lead (or other toxic metals) to add enough analyte to the ground up sample produced by this method to cause bias in the measurement of lead. Solids other than food may be suitable for use in this method. However, solid food products (such as salt, sugar, dried seeds and grains) are considered a good choice because of their grinding characteristics, low cost, availability and relative freedom from toxic contaminants. In addition, solids that are soluble in the final mix of chemicals used by the test kit are more desirable than solids that are not soluble. This is because the solid itself may be opaque enough to block the ability of the eye to see the desired color change. The volume to be used may be measured using readily available plastic or glass kitchen utensils designed for measuring out foods for recipes or may be a specially sized volume tool (spoon) to obtain the desired volume.

(3) Place the paint sample in the coffee grinder (or equivalent) and grind the solid food product plus paint sample to produce a homogenized and finely ground solid powder. Coffee grinders are cheap and readily available and, although designed to grind up coffee beans, can be used to turn many solids (such as grains, herbs, spices, etc.) into small particles. This invention utilizes this simple yet effective device to both convert the paint sample into small particles and at the same time dilute the sample within a dry solid matrix to reduce the number of lead (II) ions that are ultimately exposed to the test kit chemicals. Once ground, the mixture can be transferred to a suitable container, such as a glass or plastic tube, for temporary storage, or it can be left in the grinder.

(4) Use a specific (small) measured volume of powder from the ground material generated from the coffee grinder (the test volume) and conduct the test on this amount using the specified test kit where obtaining a specific response color is defined as a positive indicator for the presence of the metal. The test volume may be measured using readily available plastic or glass kitchen utensils designed for measuring out foods for recipes or may be a specially sized volume tool (spoon) to obtain the desired volume. Transfer the test volume into whatever container is suitable for the test kit being used such as, but not limited to a test plate, test tube, or other container, and test it using the selected test kit. The response color considered positive may be determined by observation, such as comparison to a color standard, or measured using a device such as a colorimeter as defined by the test kit being used.

There are 5 key parameters to be determined to use the invented method: (a) the size of the paint sample (from step 1); (b) the choice of the solid (food) product to use as the diluent (from step 2); (c) the volume of the solid (food) product (from step 2); (d) the duration of grinding time (from step 3); and (e) the test volume of the ground paint/food mixture to be exposed to test kit chemicals (from step 4). Other parameters, such as the chemicals used and the color that is used to indicate whether a positive or negative response is obtained are defined by the test kit technology that is being used to determine the amount of the lead in the test volume. The values for each of the above operating parameters (a), (c), (d), and (e), and the selection of the solid product (b), must be determined experimentally for each test kit. Once determined, they will remain fixed and should not require change provided that the chemical makeup of the test kit remains constant.

The operating parameters for a given test kit must be determined through replicate experimental testing. One approach used to determine the operating parameters for LBP testing for a specific test kit technology is to start with setting reasonable maximum and minimum acceptable boundaries for the values. Then, a series of small experiments is performed to explore the use of the method using these starting values with the primary goal of determining the response point using the method. It is useful to understand that the chemicals in a test kit are applied to a sample in excess of the amount needed for a stoichiometric reaction. The color response is therefore controlled by the total micrograms of lead in the subsample being tested (parameter (e), the test volume). The response point is therefore determined as the total micrograms of lead just needed to produce a positive response. Once this has been determined, the values for the above parameters (a), (c), and (e) can be adjusted mathematically so that the total effective dilution of an original sample having lead at 1.0 milligram per centimeter squared (the definition of LBP) produces a test volume lead level at the response point. Validation of the operating parameter settings is then performed using a set of paint samples having a range of different lead levels bracketing the definition of LBP.

Reasonable boundaries for the 5 key parameters for application of the invented method to LBP determinations, where LBP means paint or other surface coatings that contain lead equal to or exceeding a level of 1.0 milligram per centimeter squared are discussed below. The characteristic color change that is defined by the test kit being used is a starting point for the conduct of the experimentation used to define suitable parameters of the method with an understanding that the method will likely produce some shading or intensity gradations around the response point due to the methods ability to control the amount of lead that gets exposed to the test kit chemicals. Stated alternatively, for a given test kit, some adjustment to the intensity of the characteristic color change being designated as a positive response may be needed to ensure that the response point matches that of the action level defining a positive response. The response point is experimentally determined by examining the color intensities of the set of prepared and reacted paint samples having a range of different lead levels bracketing the definition of LBP (the action level) as discussed above.

(a) Size of the paint sample. The term size means the surface area collected. This should be big enough to ensure that the sample is representative of the painted surface undergoing testing, but not so big as to make it difficult to collect or handle using the invented method. Reasonable boundaries in terms of commonly available cork borers, which can be used to collect paint sample cores from a painted component, range from a No. 1 borer (sample area approximately 0.12 centimeters squared) to No. 12 (sample area approximately 3.3 centimeters squared).

(b) Choice of solid (food) product. The choice of the product is dependent on grinding characteristics of the product, freedom from interfering with test kit chemicals, and the product's solubility in the test kit chemicals. The desired grinding characteristics include ability to be ground into a fine powder using the coffee grinder and the food products ability to help grind paint samples into very small pieces without damaging the grinder. The characteristics also include the ability to obtain reproducible packed volumes after grinding. Grinding solids into powders entrains air into the grind making them fluffy. The variability of the total amount of lead in replicate subsamples taken from the grind must be kept to a minimum for the invented method to make accurate LBP determinations. This is accomplished by using a simple subsample packing procedure, which removes most of the entrained air when the test volume (step e) is taken from the grind. Experiments to determine the grinding characteristics of selected solid products include replicate measures of post-grinding packed volumes using the grinder at the maximum likely grind time. These replicate measures are obtained using a fixed original volume such as ¼ cup. Measuring the packed volume after grinding can be aided by transferring the grind into a graduated cylinder fitted with a plunger to pack the grind. Use of the maximum reasonable grinding time (2 minutes as discussed below) for these experiments should be sufficient to evaluate the variability of the post-grinding packed volumes for a given solid product. As discussed previously, solid products that are soluble have advantages over products that are not, but a solid such as rice may still prove viable for some test kits. Freedom from interference was found to be a more substantial issue than solubility when making a choice of product to use with the invented method. For example, dried beans are very efficient at grinding paint samples, but most contain significant amounts of iron, as do many brands of rice. The iron interferes with chemical test kits based on sulfide by forming a green precipitate (ferric iron sulfide). In addition, seed products often contain significant amounts of starch which, when exposed to test kit chemicals with high pH, creates a gel that interferes with the chemical reaction. Experiments to determine freedom from interference include, as a starting point, creating a grind without a paint sample from each solid product being investigated that has acceptable grinding characteristics using a 2 minute grinding time. A series of subsamples containing different amounts of lead is then produced from each product grind. The subsamples are created by placing a fixed volume of the grind (such as ¹⁄₁₆ or ¹⁄₃₂ teaspoon) in cells of a test plate. Then, a known mass of lead is added to each cell, on top of the subsample, using a specified small volume of an aqueous lead standard solution followed by evaporating away the added liquid using a heat lamp. After cooling, the test kit chemicals are applied to each cell to observe the response. This experiment may have to be repeated using different amounts of added lead until either: the series contains both negative and positive responses, in which case the food product is a suitable diluent; OR: it is clear that a positive response cannot be obtained with that solid product even at high lead levels, in which case it is rejected. In general, granulated sugar has been found acceptable for use with rhodizonate test kits and both sugar and salt have been found acceptable for use with sulfide test kits.

(c) Volume of the solid (food) product. The volume of the solid food product is limited by the capacity of the coffee grinder. The effective dilution of the lead in the sample is the ratio of the original volume of solid product placed in the grinder to the test volume taken out of the grind and exposed to the test kit chemicals. This dilution factor ignores differences that might exist between the volume of the solid product placed into the grinder and the total packed volume of the solid after the grinding. It also ignores any contribution of the volume of the paint sample that is ground, which is considered negligible, even for thick paint samples, provided that the volume of the food product is not too small. Since one of the requirements of EPA's ETV test program for LBP determinations includes the testing of paint with colored overlayers, the effective dilution of the sample using the invented method should be keep high enough to minimize the amount of sample in the test volume so that the paint coloring itself does not mask the test results. From a practical point of view, the minimum dilution factor is 10 and the maximum dilution factor is driven by the maximum capacity of the grinder combined with a smallest test volume that can be reproducibly collected and handled without introducing excessive amounts of variability. In addition, test volume needs to be kept as small as possible to avoid using large amounts of test kit reagents since the test reagent volume required to completely wet the subsample undergoing testing increases with increasing test volume. The maximum reasonable capacity of coffee grinders sold for home use is about ⅓ cup. The minimum reasonable test volume is 1/32 teaspoon (also known as a smidgen in food recipes). Giving consideration to minimizing use of test kit reagents as a cost savings factor, the maximum reasonable test volume is 1/16 teaspoon (also known as a pinch). Using these reasonable boundaries, the invented method using a hand-held coffee grinder is capable of achieving a dilution factor range of roughly 16 to 512.

(d) Grinding time. The grinding time needs to be long enough to ensure uniform distribution of paint particles within the test volume, but short enough to avoid excessive wear of the grinder. Coffee grinders for home use are not designed to be run for extended periods of time. Based on the amount of heat created by these grinders, 2 minutes is a reasonable maximum grind time. A reasonable minimum grind time of 30 seconds was determined by examining the amount of solid product that passed through a #35 sieve (500 micrometers or 0.5 mm) for a large number of different food products both with and without added paint samples. The paint-sample-added experimentation was considered a more difficult grinding scenario than likely to be found for testing under the EPA RRP rule in that a maximum size sample was used (cork borer No. 12) and the paint was comprised of 10 layers of newly laid oil-based paint. This is more layers than the ETV samples, and newly laid paint is less brittle than cured paint and, consequently, is harder to grind into small particles.

(e) Test volume. As discussed under (c) above, reasonable boundaries for this parameter is 1/32 teaspoon to 1/16 teaspoon.

The following 13 paragraphs illustrate one embodiment of the invented method to produce a test kit for the determination of the presence or absence of LBP. It is understood, however, that this example is not to be interpreted as limiting the scope of the invention. Those of ordinary skill in the art of conducting laboratory testing can make use of the invention by performing the steps provided below.

A series of small experiments was conducted, using the guidance discussed above, to identify suitable operating parameters for a test kit using a 6% lye pre-leach of the sample followed by addition of a nominal 6% sodium sulfide solution, which produces a dark colored solution when lead is present. The key operating parameters (a) through (e) determined through experimentation for this test kit are as follows: (a) Size of the paint sample=cork borer No. 7 (1.317 centimeters squared); (b) Choice of solid (food) product=salt; (c) Volume of the solid (food) product=2 teaspoons; (d) Grinding time=60 seconds; and, (e) Test volume=1/32 teaspoon.

The volume values above create an effective dilution factor of 64. The use of above parameters on a paint sample with a lead level of 1.0 milligram/centimeters squared generates a subsample with 20.6 micrograms of lead. The solution starts darkening at roughly 10 micrograms of lead and continues to darken into a distinct dark brown color at roughly 100 micrograms, which provides a wide range of choices to set a color at which the paint sample is considered positive. In this example, the selected color (parameter (f)) is that which matches the 20.6 micrograms of lead that is produced when the paint undergoing testing is at the definition for LBP. It is recognized that because of the gradation of color change made available by using the invented method, considerable flexibility exists to alter the settings for the operating parameters (a), (c), and (e) by simply by changing the color shade that is called a positive result.

One adaptation of the above example into an operating procedure is illustrated below. Various routine quality control and safety steps such as donning gloves, cleaning equipment and other procedures needed to eliminate cross-contamination from testing one sample to the next are not included.

(1) Collect paint sample. Fold a clean new sheet of white paper (8.5 by 11 inches) lengthwise in half to create a crease line down the center of the paper and place it open on the work surface. Use a sharp clean and dry No. 7 cork borer to obtain a sample of the paint undergoing testing and temporarily store it on a new clean sheet of white paper.

(2) Place salt in the grinder. Use a clean dry 1 tablespoon utensil and putty knife to accurately measure out 2 tablespoons of non-iodized salt into a clean dry coffee grinder. For each of the 2 aliquots of salt, pour the salt into the tablespoon so that the salt is heaped up in a pile that fills the entire spoon with excess salt piled on top. Using the flat side of the putty knife, lightly pack the salt crystals into the spoon by gently tapping on the pile of salt extending up past the sides of the spoon to ensure that the salt completely fills the spoon. Then, using the edge of the putty knife, very slowly scrape off the excess salt that extends above the lip of the spoon before pouring the contents into the coffee grinder.

(3) Place the paint sample in the grinder. Using the fold in the paper holding the paint sample as a channel to direct the movement of the sample when the paper is tipped, transfer the paint sample to the grinder so that it sits on top of the salt already in the grinder. Toss the sheet of paper in the trash.

(4) Grind the paint sample. Place the lid on the grinder and grind the sample for 60 seconds. While grinding, sharply tap the lid of the grinder (taking care not to damage it) about every 10 seconds using the handle end of the putty knife (holding the blade end in your hand) to aid the mixing and grinding process. Allow the grinder to sit unopened for about 2 minutes to allow the fine particles created during grinding to settle.

(5) Transfer the grind to a collection bottle. Fold a clean new sheet of white paper (8.5 by 11 inches) lengthwise in half to create a crease line down the center of the paper and place it open on the work surface for use as a catch tray for the grind coming out of the grinder. Invert the coffee grinder with the lid still in place and sharply slap the side of the grinder 3 times to dislodge as much ground material as possible into the lid of the grinder. While still inverted, hold the grinder over the folded paper and gently pull off the lid. Place the body of the grinder to the side. The small amount of grind sticking to the inside body of the grinder can be ignored. Slowly invert the lid over the center of the paper spilling the bulk of the grind into the paper. While holding the lid open side down, sharply tap the thicker sides of the lid of the grinder (taking care not to damage it) using the handle end of the putty knife (holding the blade end in your hand) to dislodge as much grind as possible from the lid. The small amount of grind sticking to the inside body of the lid after tapping can be ignored. Place the lid of the grinder to the side (to be cleaned later along with the grinder before use on the next sample). Using the fold in the paper holding the grind as a channel to direct the movement of the sample when the paper is tipped, transfer the grind to a 50 mL plastic screw cap tube or equivalent container. Toss the paper into the trash.

(6) Obtain a subsample (test volume) for testing. Hold the tube containing the grind horizontally so the lid of the tube is on its side and very slowly rotate the tube between your fingers so that the grind in the tube can be seen tumbling over itself like clothes in a dryer. Alternatively, you can slowly roll the tube across the work surface to achieve this tumbling. Rotate the tube so that it rolls over at least 5 complete times. The purpose of this is to aid in distributing the paint particles evenly throughout the grind. Do not shake the tube as shaking tends to aggregate particles in the grind by size. Place the tube into a rack or block to hold it upright with the lid at the top. Unscrew the lid and place it to the side. Using the test volume spoon, reach into the container and scoop up a sample of the grind so that the spoon presses against the wall of the container at the end of the scooping motion to pack the grind into the spoon. Tilt the container as needed to reach the grind. Repeat this scooping up and trapping the grind between the spoon and the container wall a total of 3 times without removing the spoon from the container. This will ensure that the grind will become packed tightly in the spoon. On the last of the 3 scooping motions, ensure that the grind in the spoon extends over the top of the sides of the spoon. Using the clean flat side of the putty knife, press down on the grind in the spoon to complete packing of the grind in the test volume. Then, using the edge of the putty knife, very slowly scrape off the excess grind that extends above the lip of the spoon.

(7) Place the test volume into a clear small (3 mL) polystyrene test tube. Place the test tube into a rack or block to hold it upright as needed here and in the following steps. Pour the grind packed in the spoon into the test tube and lightly tap the test tube on the work surface to move the subsample to the bottom of the tube. If needed, a clean plastic micro funnel can be used to ensure that all of grind packed in the spoon gets into the test tube.

(8) Conduct the pre-leach of the subsample. Place 0.5 mL of 6% lye solution into the test tube, cap the tube and shake gently to mix. Allow to stand for 3 minutes.

(9) Add the coloring reagent to the subsample. Place 0.5 mL of a 6% sulfide solution into the test tube, cap the tube and shake gently to mix.

(10) Make the LBP determination. Using the turning point color shown on a color card, compare the color of the solution in the test tube (ignore any solids present in the bottom) to the color card. A solution color equal to or darker than the color card is positive for LBP. All colors lighter than the color card are negative for LBP.

That which is claimed is:

1. A method for reducing a sensitivity of a chemical test kit for detecting lead-based paint to increase a concentration of lead in a paint sample at which the chemical test kit generates a positive response, the method comprising the following steps:
    (a) providing a chemical test kit for detecting lead-based paint wherein the chemical test kit has one or more test kit chemicals to induce a chemical reaction on exposure of a paint sample to the one or more test kit chemicals with a positive response at a predetermined concentration of lead in a paint sample, the positive response indicative of a presence of lead in the paint sample equal to or exceeding the predetermined concentration, and a negative response indicative a lack of lead in the paint sample equal to or exceeding the predetermined concentration;
    (b) providing a paint sample with a known surface area;
    (c) providing a diluent of known volume wherein the diluent comprises a solid, dry material;
    (d) providing a grinding device;
    (e) placing the diluent of known volume into the grinding device;
    (f) placing the paint sample into the grinding device on top of at least a portion of the diluent;
    (g) actuating the grinding device for a given period of time thereby grinding the diluent and the paint sample to produce a volume of a dry, solid matrix of grind material that exhibits a positive response on exposure to the one or more test kit chemicals at a higher concentration of lead in the paint sample that is higher than the predetermined concentration level of lead in a paint sample of the chemical test kit;
    (h) collecting a test volume of material from the dry, solid matrix of grind material in the grinding device;
    (i) exposing the test volume of material while in a dry, solid matrix to the one or more test kit chemicals; and
    (j) observing the test volume of material after exposing the test volume of material to the one or more test kit chemicals to determine whether the chemical reaction induced a positive response at the higher concentration of lead in the paint sample or a negative response.

2. The method of claim 1 wherein the diluent comprises sugar or salt.

3. The method of claim 1 wherein the diluent comprises a dry food product.

4. The method of claim 1 wherein the diluent is soluble in the one or more test kit chemicals.

5. The method of claim 1 wherein the paint sample comprises a solid paint coating.

6. The method of claim 1 further comprising the step of placing the volume of grind material into a container prior to collecting the test volume.

7. The method of claim 1 further comprising the step of tumbling the volume of grind material within the container prior to the step of collecting the test volume of material.

8. The method of claim 1 further comprising the step of placing the test volume of material in a container prior to exposing the test volume of material to the one or more test chemicals.

9. The method of claim 1 wherein the one or more test chemicals of the chemical test kit comprises rhodizonate.

10. The method of claim 1 wherein the one or more test chemicals of the chemical test kit comprises sulfide.

11. The method of claim 1 wherein the diluent comprises sugar or salt and wherein the one or more test chemicals of the chemical test kit comprise a caustic solution and a sulfide solution.

12. The method of claim 1 wherein the positive response of the chemical test kit is based on a comparison standard.

13. The method of claim 12 wherein the positive response of the chemical test kit is based on one or more characteristic color changes.

14. The method of claim 13 wherein the step of observing the test volume of material after exposing the test volume of material to the one or more test kit chemicals to determine whether the chemical reaction induced a positive response at the higher concentration of lead in the paint sample or a negative response comprises determining an optical density value of the test volume of material with a colorimeter wherein optical density values at or above a specified level are considered positive responses and optical density values below a specified level are considered negative responses.

15. A method for reducing a sensitivity of a chemical test kit for detecting lead-based paint to increase a concentration of lead in a sample at which the chemical test kit generates a positive response, the method comprising the following steps:
    (a) providing a chemical test kit for detecting lead-based paint wherein the chemical test kit has one or more test kit chemicals to induce a chemical reaction on exposure of a sample to the one or more test kit chemicals with a positive response at a predetermined concentration of lead in a paint sample, the positive response indicative of a presence of lead in the sample equal to or exceeding the predetermined concentration, and a negative response indicative a lack of lead in the sample equal to or exceeding the predetermined concentration;
    (b) providing a sample with a known surface area, mass, or volume;
    (c) providing a diluent of known volume wherein the diluent comprises a solid, dry material;
    (d) providing a portable grinding device;
    (e) placing the diluent of known volume into the grinding device;
    (f) placing the sample into the grinding device on top of at least a portion of the diluent;
    (g) actuating the grinding device for a given period of time thereby grinding the diluent and the sample to produce a volume of a dry, solid matrix of grind material that exhibits a positive response on exposure to the one or more test kit chemicals at a higher concentration of lead in the sample that is higher than the predetermined concentration level of lead in a sample of the chemical test kit;
    (h) collecting a test volume of material from the dry, solid matrix of grind material in the grinding device;
    (i) exposing the test volume of material while in a dry, solid matrix to the one or more test kit chemicals; and
    (j) observing the test volume of material after exposing the test volume of material to the one or more test kit chemicals to determine whether the chemical reaction induced a positive response at the higher concentration of lead in the sample or a negative response.

16. The method of claim 15 wherein the diluent comprises sugar or salt.

17. The method of claim 15 wherein the diluent is soluble in the one or more test kit chemicals.

18. The method of claim 15 wherein the sample comprises a solid material.

19. The method of claim 15 further comprising the step of placing the volume of grind material into a container prior to collecting the test volume.

20. The method of claim 15 further comprising the step of tumbling the volume of grind material within the container prior to the step of collecting the test volume of material.

21. The method of claim 15 further comprising the step of placing the test volume of material in a container prior to exposing the test volume of material to the one or more test chemicals.

22. The method of claim 15 wherein the grinding device comprises a coffee bean grinder.

23. The method of claim 15 wherein the positive response of the chemical test kit is based on a comparison standard.

24. The method of claim 23 wherein the positive response of the chemical test kit is based on one or more characteristic color changes.

25. The method of claim 24 wherein the step of observing the test volume of material after exposing the test volume of material to the one or more test kit chemicals to determine whether the chemical reaction induced a positive response at the higher concentration of lead in the sample or a negative response comprises determining an optical density value of the test volume of material with a colorimeter wherein optical density values at or above a specified level are considered positive responses and optical density values below a specified level are considered negative responses.

* * * * *